(12) United States Patent
Davidzon et al.

(10) Patent No.: US 11,242,506 B2
(45) Date of Patent: Feb. 8, 2022

(54) METHODS AND APPARATUS FOR SEPARATING CELLS FROM MICROCARRIERS

(71) Applicant: Mesoblast International Sàrl, Meyrin (CH)

(72) Inventors: Normand Davidzon, Melbourne (AU); Paul Simmons, Melbourne (AU)

(73) Assignee: MESOBLAST INTERNATIONAL SÁRL, Meyrin (CH)

(*) Notice: Subject to any disclaimer, the term of this patent is extended or adjusted under 35 U.S.C. 154(b) by 294 days.

(21) Appl. No.: 15/575,160

(22) PCT Filed: May 27, 2016

(86) PCT No.: PCT/EP2016/062016
§ 371 (c)(1),
(2) Date: Nov. 17, 2017

(87) PCT Pub. No.: WO2016/193150
PCT Pub. Date: Dec. 8, 2016

(65) Prior Publication Data
US 2018/0142201 A1 May 24, 2018

(30) Foreign Application Priority Data

May 29, 2015 (AU) .............................. 2015901998

(51) Int. Cl.
*C12M 1/00* (2006.01)
*C12M 1/26* (2006.01)
(Continued)

(52) U.S. Cl.
CPC ............. *C12M 47/02* (2013.01); *B01D 33/01* (2013.01); *B01D 33/0108* (2013.01);
(Continued)

(58) Field of Classification Search
CPC ...... C12M 47/02; C12M 25/16; C12M 27/02; C12M 33/14; B01D 33/01; B01D 35/0276; B01D 39/12; B01D 33/0108
See application file for complete search history.

(56) References Cited

U.S. PATENT DOCUMENTS 4,062,773 A * 12/1977 Leonard .............. A61M 1/3627
210/780
2003/0143727 A1    7/2003 Chang
(Continued)

FOREIGN PATENT DOCUMENTS

CN    1260343 C    6/2006
CN    101775364 A    7/2010
(Continued)

OTHER PUBLICATIONS

International Search Report dated Aug. 19, 2016 in connection with PCT International Application No. PCT/EP2016/062016.
(Continued)

*Primary Examiner* — Liam Royce
(74) *Attorney, Agent, or Firm* — John P. White (57) ABSTRACT

An apparatus for separating cells from microcarriers comprises a chamber having a body and a base. The chamber is configured to receive a mixture comprising cells and microcarriers. The apparatus further comprises a filtration element disposed within the chamber and coupled to the body. The filtration element is configured to filter microcarriers from the mixture. The apparatus further comprises an adjustment mechanism coupled to the chamber. The adjustment mechanism is configured for selective extension and retraction of at least a portion of the body of the chamber to move the filtration element relative to the base of the chamber.

10 Claims, 10 Drawing Sheets

(51) Int. Cl.
*C12M 1/12* (2006.01)
*B01D 35/027* (2006.01)
*B01D 33/01* (2006.01)
*B01D 39/12* (2006.01)
*C12M 1/06* (2006.01)

(52) U.S. Cl.
CPC ......... *B01D 35/0276* (2013.01); *B01D 39/12* (2013.01); *C12M 25/16* (2013.01); *C12M 27/02* (2013.01); *C12M 33/14* (2013.01)

(56) References Cited

U.S. PATENT DOCUMENTS

| | | |
|---|---|---|
| 2004/0058436 A1 | 3/2004 | Zhang |
| 2007/0224676 A1 | 9/2007 | Haq |
| 2010/0065488 A1* | 3/2010 | Milne ............... B01D 35/05 210/242.1 |
| 2013/0081995 A1 | 4/2013 | Larsen |
| 2014/0110356 A1* | 4/2014 | McKay ............... A61F 2/28 210/780 |

FOREIGN PATENT DOCUMENTS

| | | |
|---|---|---|
| CN | 201933090 U | 8/2011 |
| CN | 102337200 A | 2/2012 |
| CN | 202415566 U | 9/2012 |
| JP | H01-168273 | 11/1989 |
| JP | H06-296274 A | 9/1994 |
| JP | 2001-509675 | 7/2001 |
| JP | 2003-235539 | 8/2003 |
| JP | 2010-252635 | 11/2010 |

OTHER PUBLICATIONS

Written Opinion of the International Searching Authority dated Aug. 19, 2016 in connection with PCT International Application No. PCT/EP2016/062016.
English translation of Feb. 25, 2020 Office Action issued in connection with Japanese patent application No. 2017-561851.
Chinese official action (and machine translation thereof into English) dated Nov. 4, 2020 in corresponding Chinese Patent Application No. 201680031179.4.

* cited by examiner

Exhibit B

METHODS AND APPARATUS FOR SEPARATING CELLS FROM MICROCARRIERS

CROSS-REFERENCE TO RELATED APPLICATIONS

This application is a § 371 national stage of PCT International Application No. PCT/EP2016/062016, filed May 27, 2016, claiming priority of Australian Patent Application No. AU 2015901998, filed May 29, 2015, the contents of each of which are hereby incorporated by reference into the application.

TECHNICAL FIELD

Described embodiments relate to methods and apparatus for separating cells from microcarriers.

BACKGROUND

Microcarrier technology is employed to cultivate cells in bioreactors. In particular, microcarriers act as support matrices to allow anchorage dependent cells to grow in culture.

Conventional methods of separating cells from microcarriers may be costly and time consuming, involving allowing the cells and microcarriers suspended in medium to settle toward a base of the bioreactor, introducing an enzyme to the bioreactor, agitating the mixture to cause the cells to detach or release from the microcarriers and subsequently, passing the mixture through a filter to separate the cells from the microcarriers.

Accordingly, it is desired to address or ameliorate one or more shortcomings of such prior art methods or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to an apparatus for separating cells from microcarriers, the apparatus comprising a chamber having a body and a base, the chamber configured to receive a mixture comprising cells and microcarriers; a filtration element disposed within the chamber and coupled to the body, the filtration element configured to filter microcarriers from the mixture; and an adjustment mechanism coupled to the chamber, the adjustment mechanism configured for selective extension and retraction of at least a portion of the body of the chamber to move the filtration element relative to the base of the chamber.

In some embodiments, selective extension of the at least a portion of the body of the chamber in response to selective actuation of the adjustment mechanism may cause the at least a portion of the body to extend away from the base of the chamber and selective retraction of the at least a portion of the body of the chamber in response to selective actuation of the adjustment mechanism may cause the at least a portion of the body to retract toward the base of the chamber.

In some embodiments, selective extension of the at least a portion of the body of the chamber in response to selective actuation of the adjustment mechanism may cause the filtration element to move away from the base of the chamber and selective retraction of the at least a portion of the body of the chamber in response to selective actuation of the adjustment mechanism may cause the filtration element to move towards the base of the chamber.

For example, the chamber may be configured to transition between an extended state and a retracted state in response to selective actuation of the adjustment mechanism.

The filtration element may comprise a filter configured to allow cells to pass through the filter and to block microcarriers from passing through the filter. The filtration element may comprise a filter base configured to cooperate with the base of the chamber to allow the filter base to sit flush with the base of the chamber when the apparatus is in a retracted state.

The body may be an elongate body and the base may be a conical base. In some embodiments, the body may include bellows to allow for expansion and contraction of the body. The body may be composed of a flexible material.

The adjustment mechanism may comprise one or more actuators. For example, the one or more actuators comprise one or more electric cylinders. In some embodiments, the one or more actuators are coupled to the body of the chamber. In some embodiments, the chamber comprises a cover coupled to an first end of the body and the one or more actuators are coupled to the cover.

In some embodiments, the apparatus may further comprise an agitation mechanism to instigate agitation of a mixture within the chamber. For example, the agitation mechanism may comprise at least one of a vibration table, a drop cam and air.

Some embodiments relate to a bioreactor comprising the apparatus described above and an agitation system to agitate a mixture within the chamber. The agitation system may comprise one or more impellers.

Some embodiments relate to a method for separating cells from microcarriers, the method comprising: introducing a mixture comprising cells and microcarriers to the filtration element of the apparatus described above when the apparatus is in an extended state; retaining microcarriers and cells attached to microcarriers in the filtration element; actuating the adjustment mechanism to move the filtration element toward the base of the chamber; introducing an agent for facilitating detachment of the cells from the microcarriers to the chamber; agitating the mixture in the chamber to detach at least some of the cells from the microcarriers; and retaining the microcarriers in the filtration element and allowing the detached cells and agent to pass through the filtration element.

In some embodiments, the mixture may further comprise media and retaining microcarriers and cells attached to microcarriers in the filtration element may further comprise conveying media from the chamber.

In some embodiments, the agent for facilitating detachment of the cells from the microcarriers to the chamber may be introduced to the chamber via a port disposed in the base of the chamber. The method may further comprise conveying air to the chamber to assist in facilitating the mixing of the agent, cells and microcarriers.

In some embodiments, the method may further comprise conveying the agent and the detached cells from the chamber to a second chamber of a second apparatus. The method may further comprise conveying convey air to the chamber to assist in facilitating the conveying of the agent and detached cells from the chamber. The method may further comprise conveying buffer to the chamber to assist in facilitating the conveying of the agent and detached cells from the chamber. In some embodiments, the method comprises introducing an agent inhibitor to the second chamber to inhibit activity of the agent.

In some embodiments, the method may further comprise actuating the adjustment mechanism to move the filtration element away from the base of the chamber; and introducing an inhibitor to the chamber to inhibit activity of the agent. The method may comprise conveying buffer to the chamber to rinse the filtration element and chamber.

The method may comprising conveying the detached cells to a collection receptacle.

Some embodiments relate to a method for separating cells from microcarriers, the method comprising introducing a mixture comprising cells and microcarriers to the filtration element of the apparatus described above; retaining microcarriers and cells attached to microcarriers in the filtration element; introducing an agent for facilitating detachment of the cells from the microcarriers to the chamber; agitating the mixture in the chamber to detach at least some of the cells from the microcarriers; retaining the microcarriers in the filtration element and allowing the detached cells and agent to pass through the filtration element; actuating the adjustment mechanism to move the filtration element away from the base of the chamber; and introducing an inhibitor to the chamber to inhibit activity of the agent.

Some embodiments relate to a method for separating cells from microcarriers, the method comprising introducing a mixture comprising cells and microcarriers to the filtration element of the apparatus described above; retaining microcarriers and cells attached to microcarriers in the filtration element; introducing an agent for facilitating detachment of the cells from the microcarriers to the chamber; agitating the mixture in the chamber to detach at least some of the cells from the microcarriers; and retaining the microcarriers in the filtration element and allowing the detached cells and agent to pass through the filtration element.

The method may comprise actuating the adjustment mechanism to move the filtration element away from the base of the chamber and introducing an inhibitor to the chamber to inhibit activity of the agent.

In some embodiments, the mixture may be introduced to the apparatus when the apparatus is in an extended state and the method may comprise actuating the adjustment mechanism to move the filtration element toward the base of the chamber before introducing the agent to the chamber.

In some embodiments, the mixture may comprise media and retaining microcarriers and cells attached to microcarriers in the filtration element may further comprise conveying media from the chamber.

Some embodiments relate to use of the apparatus described above to separate cells from microcarriers.

Some embodiments relate to use of the bioreactor described above to separate cells from microcarriers.

Some embodiments relate to use of the bioreactor described above to exchange pre-set volumes of media during a mixing process.

DESCRIPTION OF EMBODIMENTS

Described embodiments relate to methods and apparatus for separating cells from microcarriers. In some embodiments, the apparatus comprises a chamber for receiving a mixture, such as media, cells and microcarriers, and a filtration element to filter the microcarriers from the mixture. The chamber may comprise a base and an adjustable body capable of being extended and retracted. The filtration element may be directly or indirectly attached or coupled to the body. An adjustment mechanism may be provided, which, when actuated, is configured to cooperate with the chamber to cause the selectable extension and retraction of at least a portion of the body of the chamber and the movement of the filtration element away from and toward the base of the chamber, respectively. In this way, the chamber may be selectively adjusted enabling the chamber to be employed for various processes as described below. In some embodiments, the apparatus may be employed for performing methods of separating cells from microcarriers. In some embodiments, the apparatus may be employed as a bioreactor. In some embodiments, the apparatus may be employed as a bioreactor and may be employed for performing methods of separating cells from microcarriers and/or other bioreactor processes including perfusion and washing.

Figure 1A:
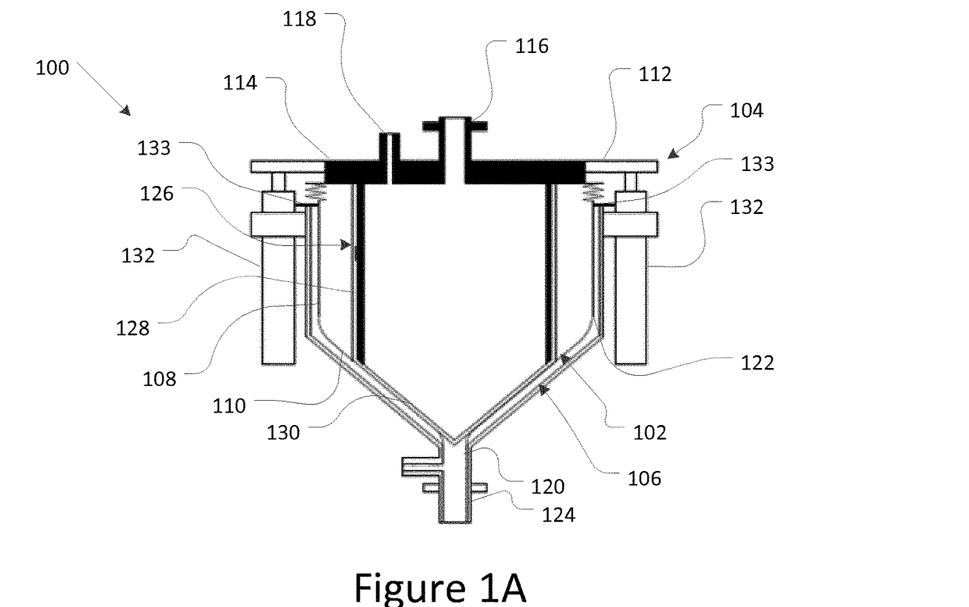
FIG. 1A is a front view of an apparatus for separating cells from microcarriers, according to some embodiments.
Figure 1B:
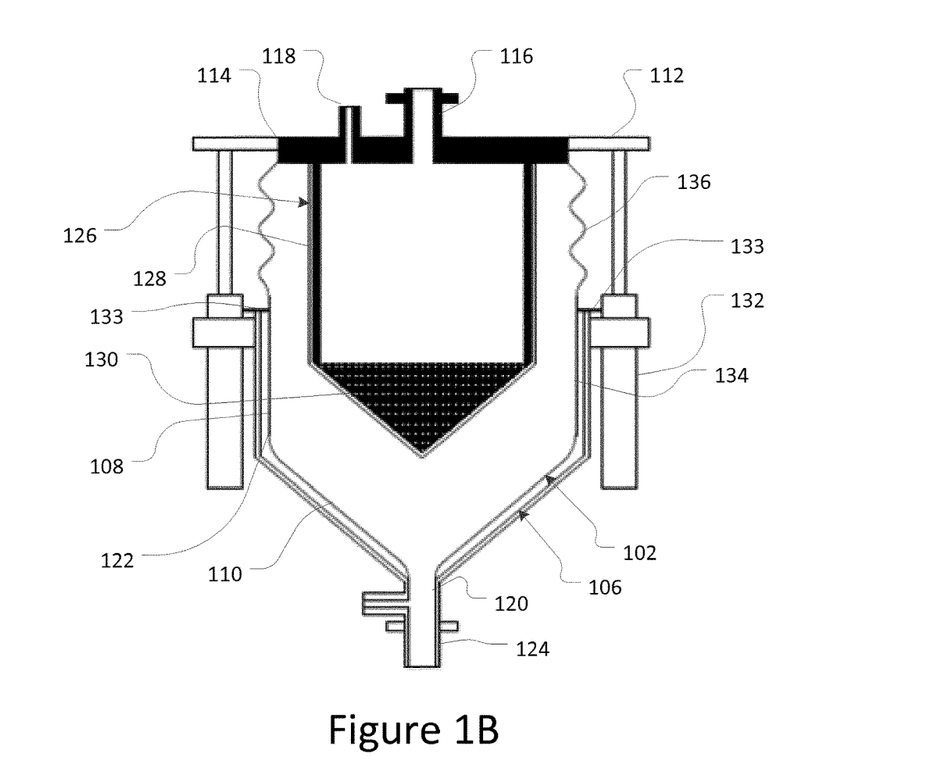
FIG. 1B is a front view of the apparatus of FIG. 1A in an extended state, according to some embodiments.

Referring to FIGS. 1A and 1B, there is illustrated an apparatus 100 for separating cells from microcarriers, according to some embodiments. The apparatus 100 comprises a chamber 102 for receiving and containing mixtures and an adjustment mechanism 104 to allow for selective adjustment of the chamber 102. In some embodiments, the apparatus 100 may comprise a housing 106 for receiving the chamber 102. The housing 106 may be a container or receptacle configured to cooperatively receive the chamber 102.

The chamber 102 may comprise a body 108 and a base 110. The body 108 may be substantially elongate and the base 110 may taper from the body 108. For example, the body 108 may be a substantially cylindrical body and the base 110 may be a substantially conical base. In some embodiments, the chamber 102 may comprise a cover or lid 112 coupled or attached to a first end 114 of the body 108 of the chamber 102. In some embodiments, the cover 112 may comprise a disc.

The body 108 may be extendible and retractable or contractible along its length. For example, the body 108 may be composed of a pliable, stretchable or flexible material, such as a flexible material, to allow the body 108 to be extended and retracted or compressed. In some embodiments, the body 108 may be provided with bellows or corrugations (not shown) to allow for expansion and contraction of the body 108. In some embodiments, the adjustment mechanism 104 is coupled or attached to the chamber 102 and the body 108 may be extended or retracted with respect to the base 110 in response to actuation of the adjustment mechanism 104 as discussed in more detail below.

The chamber 102 may comprise an inlet/outlet or port 116 to allow for fluid communication between the chamber 102 and a conduit (not shown) to be connected thereto. For example, in some embodiments, the inlet/outlet or port 116 may be provided toward or at the first end 114 of the chamber 102 and may extend through the cover 112. The inlet/outlet or port 116 may be provided to allow biomass to be conveyed to the chamber 102. In some embodiments, an inlet 118 may also be provided to allow fluids, such as air and/or buffer to be conveyed to the chamber 102. For example, the inlet 118 may be disposed toward or at the first end 112 of the body 108 of the chamber 102 and may extend through the cover 112.

The chamber 102 may comprise an inlet/outlet or port 120 to allow for fluid communication between the chamber 102 and a conduit (not shown) to be connected thereto. For example, in some embodiments, the inlet/outlet or port 120 may be provided at the base 110 of the chamber 102 and the base 110 may taper from a second end 122 of the body 108 toward the port 120. In some embodiments, the housing 106 may also comprise an inlet/outlet or port 124 arranged to cooperate with port 110 to allow for fluid communication between the chamber 102 and the conduit (not shown) to be connected thereto.

As depicted in FIGS. 1A and 1B, the apparatus 100 may comprise a filtration element 126, such as a filtration bag, disposed within the chamber 102 and in fluid communication with the port 116 and the inlet 118, if present. The filtration element 126 may comprise side walls 128 and a filter base 130, such as a tapered or conical base, extending from the side walls 128. The filter base 130 may comprise or be composed of a mesh filter. For example, the mesh filter may be configured or sized to allow cells to pass through the mesh filter and to filter or block microcarriers from passing through the mesh filter.

The filtration element 126 may be directly coupled or attached to the body 108 of the chamber, for example, at the first end 114 of the body 108, and/or to the cover 112 of the chamber 102.

As shown in FIGS. 1A and 1B, in some embodiments, the adjustment mechanism 104 may comprise one or more actuators 132. For example, the one or more actuators 132 may comprise electric cylinders or mechanical actuators, such as cams.

The one or more actuators 132 may be directly or indirectly coupled to the body 108 of the chamber 102. In some embodiments, the one or more actuators 132 may be coupled to the first end 114 of the body and/or the cover 112 of the chamber 102 and the body 108 may be configured to move relative to the base 110 of the chamber 102, for example, to move away from or toward the base 110 of the chamber 102, in response to selective actuation of the one or more actuators 132.

In some embodiments, the adjustment mechanism 104 may be fixedly coupled to or attached to the body 108 of the chamber 102 at a region located between the first end 114 and the second end 122 of the body 108, for example, by one or more flanges 133. The body 108 may therefore comprise a relatively fixed section 134 in proximity to the second end 122 of the body 108 and a relative adjustable section 136 in proximity to the first end 114 of the body 108. For example, the relative adjustable section 136 may be configured to extend and retract in response to actuation of the one or more actuators 132.

Actuation of the one or more actuators 132 to cause the first end 114 of the body 108 of the chamber 102 to move toward the base 110 may cause at least a portion of the body 108 of the chamber 102, for example, the relatively adjustable section 136, to retract or contract and cause the filtration element 126 to be moved toward the base 110 of the chamber 102, as illustrated in FIG. 1A. Similarly, actuation of the actuators 132 to cause the first end 114 of the body 108 of the chamber 102 to move away from the base 110 may cause at least a portion of the body 108 of the chamber 102, for example, the relative adjustable section 136, to extend and cause the filtration element 126 to be moved away from the relatively fixed section 134 and/or the base 110 of the chamber 102, as illustrated in FIG. 1B.

Thus, in response to actuation of the one or more actuators 132, the chamber 102 may assume an at least partially or fully retracted or contracted state, as shown in FIG. 1A, and an at least partially or fully extended or expanded state, as shown in FIG. 1B. The adjustment mechanism 104 enables the chamber 102 to transition between a fully retracted state, a partially retracted state, a partially extended state and a fully extended state and thereby move the filtration element 126 toward and away from the base 110 of the chamber 102.

An overall length of the filtration element 126 may be less than an overall length of the chamber 102. In some embodiments, the length of the side walls 128 of the filtration element 126 is less than the length of the body 108 of the chamber 102. In some embodiments, the filter base 130 is configured to cooperate with the base 110 to allow the filter base 130 to sit flush or substantially flush with the base of the chamber 102 when the apparatus 100 is in the retracted or compressed state.

In some embodiments, the apparatus 100 comprises an agitation mechanism 338 (FIG. 3) to instigate agitation or mixing of a mixture within the chamber 104. For example, the agitation mechanism 338 may comprise a vibration table, a drop cam and/or air.

Figure 2A:
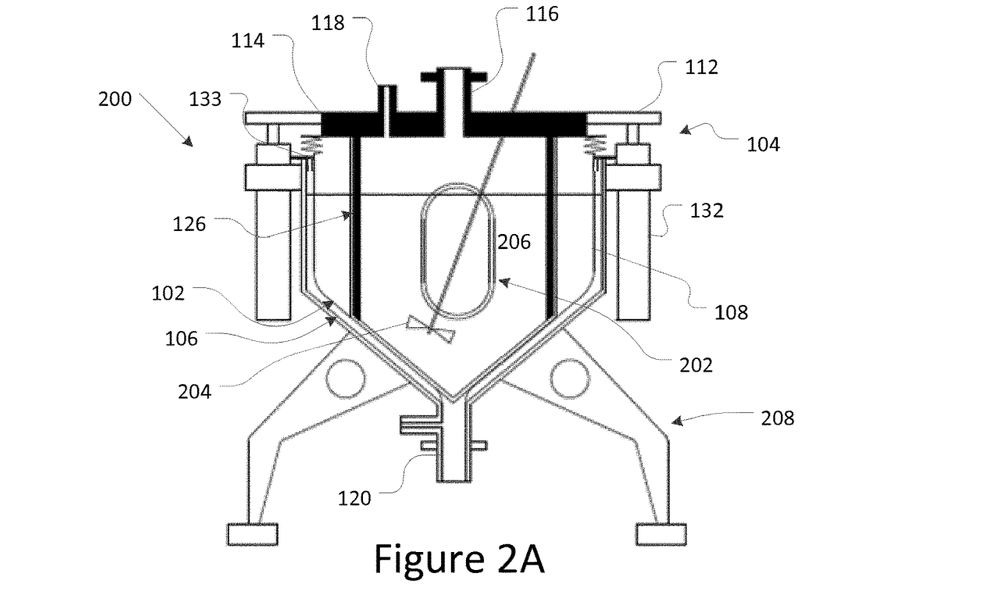
FIG. 2A is a front view of an apparatus for separating cells from microcarriers, according to some embodiments.
Figure 2B:
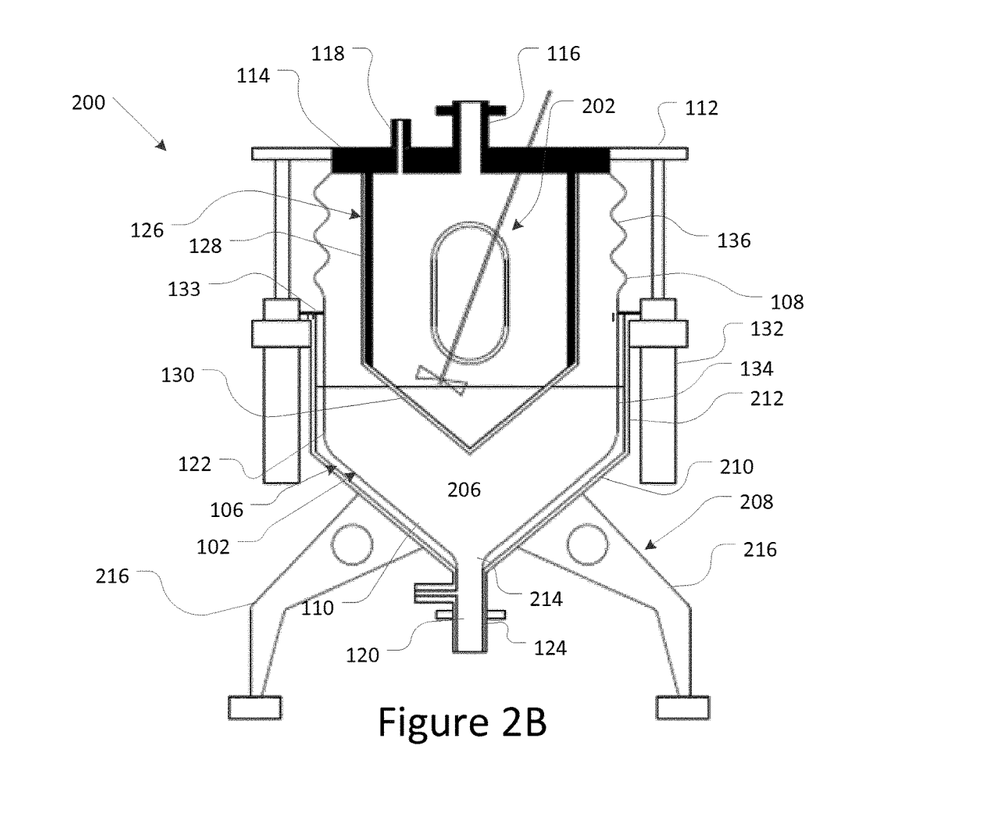
FIG. 2B is a front view of the apparatus of FIG. 2A in an extended state, according to some embodiments.

Referring to FIGS. 2A and 2B, there is illustrated an apparatus 200 for separating cells from microcarriers, according to some embodiments. The apparatus 200 comprises similar components and elements to those of apparatus 100 depicted in FIGS. 1A and 1B and accordingly those similar components and elements are denoted like numerals.

In some embodiments, the apparatus 200 may be a bioreactor. For example, the apparatus 200 may be employed as a bioreactor and may comprise an agitation system 202 including an impeller 204. In some embodiments, the agitation system 202 may be configured to agitate a mixture 206 retained within the filtration element 126 of the chamber 102. For example, the impeller 204 may be disposed within the filtration element 126 of the chamber 102. In some embodiments, the impeller 204 may be coupled to the first end 114 of the body 108 and/or to the cover 112 of the chamber 212 and may be configured to move with the filtration element 126 relative to the base 110 of the chamber 102 in response to actuation of the adjustment mechanism 104. The apparatus 200 may or may not include the agitation mechanism 338 of apparatus 100.

In some embodiments, the apparatus 200 may comprises a support structure 208 for receiving the chamber 102. For example, the support structure 208 may comprise a seat 210, such as a conical shaped seat, for receiving the base 110 of the chamber 102 and walls 212 for receiving at least a portion of the body 108 of the chamber 102. An aperture 214 may be disposed in the seat 210 to accommodate the port 120 of the chamber 102 and the port 124 of the housing 106. In some embodiments, the support structure 208 may also comprise legs 216 to allow for elevation of the seat 210 and accordingly, the chamber 102.

In some embodiments, the base 110 of the chamber 104 may be configured to adhere to the seat 210 of the support structure 208. In some embodiments, an adhesive (not shown) is provided on an external surface of the base 110 and/or an internal surface of the seat 210. In some embodiments, a vacuum port (not shown) is disposed in the support structure 208 and may be configured to connect to a vacuum pump to thereby provide suction to attract and adhere the base 110 to the seat 210.

In some embodiments, the housing 106 may comprise an adjustable base (not shown) capable of selectively transitioning between a tapered or conical shaped base and a platform base which may be substantially flat. The base 110 of the chamber 102 may be configured to cooperate with the adjustable base such that the base 110 becomes compressed to conform with the housing when it assumes or has transitioned to the platform base.

Figure 3:
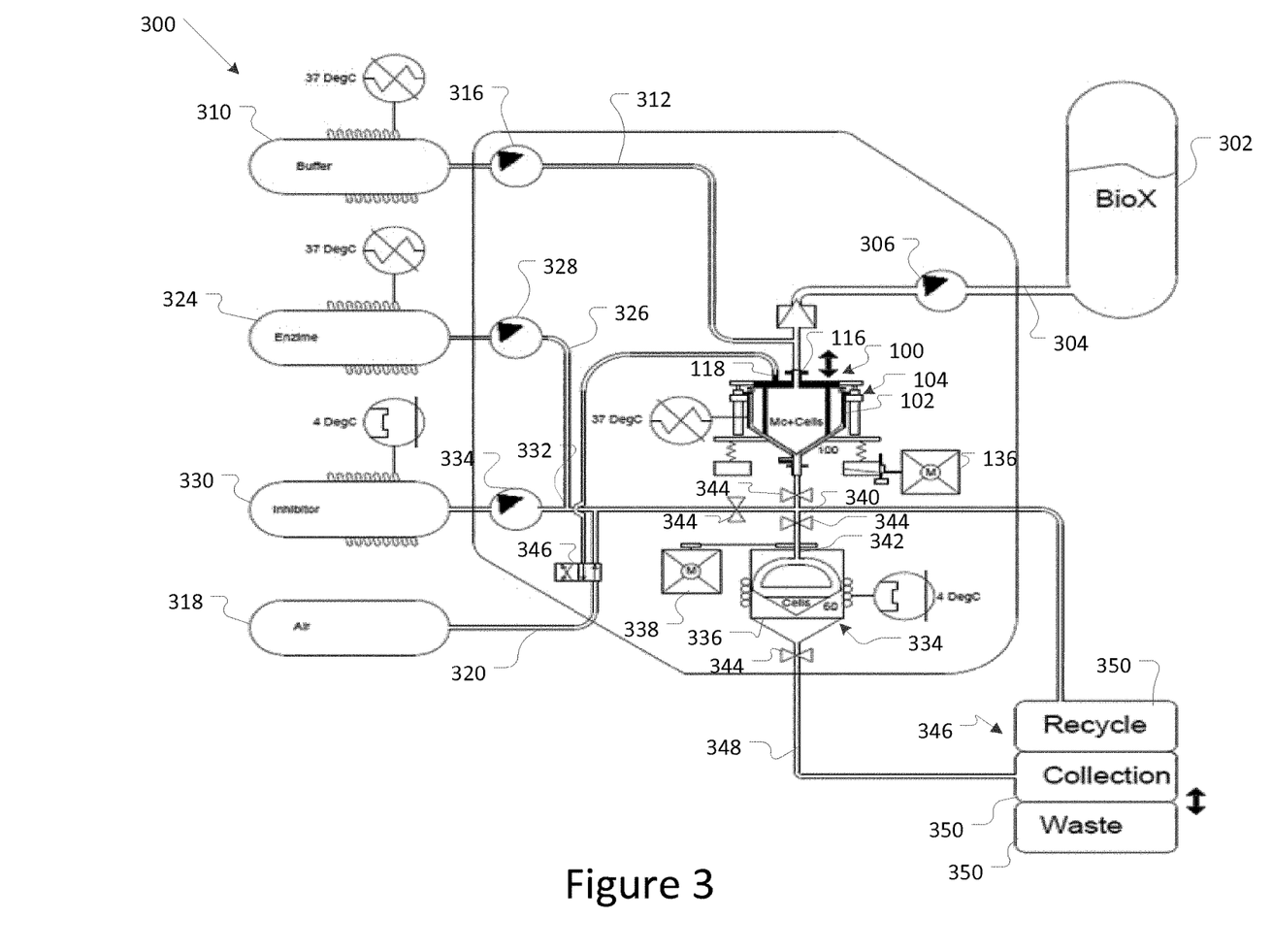
FIG. 3 is a schematic view of an assembly for separating cells from microcarriers including the apparatus of FIGS. 1A and 1B, according to some embodiments.

Referring to FIG. 3, there is illustrated a schematic overview of an assembly 300 for separating cells from microcarriers according to some embodiments. The assembly 300 comprises the apparatus 100 in fluid communication with a bioreactor 302 via a bioreactor fluid conduit 304 disposed between the bioreactor 302 and the port 116 of the chamber 102. For example, a bioreactor pump 306 may be provided in the fluid conduit 304 to convey biomass from the bioreactor 302 to the chamber 102 of the apparatus 100. In some embodiments, the chamber 102 is configured to maintain content provided therein at a temperature of approximately 37° C. In some embodiments, the chamber 102 may be housed in a housing (not shown) to facilitate maintenance of content of the chamber 102 at a desired temperature and/or connection to other fluid conduits.

The assembly 300 may further comprise a buffer tank 310 in fluid communication with the chamber 102 of the apparatus 100 via a buffer fluid conduit 312 disposed between the buffer tank 310 and port 116 of the chamber 102. For example, a buffer pump 316 may be provided in the buffer fluid conduit 312 to convey buffer from the buffer tank 310 to the chamber 102 of the apparatus 100. In some embodiments, the buffer tank 310 is configured to store buffer at a set temperature, for example, approximately 37° C.

The assembly 300 may further comprise an air tank 318 in fluid communication with the chamber 102 of the apparatus 100 via an air conduit 320 disposed between the air tank 318 and the inlet 118 of the chamber 102.

The assembly 300 may further comprise an agent tank 324 in fluid communication with the port 120 of the chamber 102 of the apparatus 100 via an agent fluid conduit 326 and conduit 332. An agent pump 328 may be provided in the agent fluid conduit 326 to convey agent from the agent tank 324 to the chamber 102 of the apparatus 100. In some embodiments, the agent tank 324 is configured to store agent at a set temperature, for example, approximately 37° C. For example, the agent may be a detachment agent. In some embodiments, the detachment agent may comprise an enzyme, such as Trypsin. In some embodiments, the detachment agent may comprise a non-enzymatic agent, such as a cation chelator.

The assembly 300 may further comprise an inhibitor tank 330. The inhibitor tank 330 may be in fluid communication with the chamber 102 of the apparatus 100 via the fluid conduit 332 disposed between the inhibitor tank 330 and the port 120 of the chamber 104. For example, an inhibitor pump 334 may be provided in the fluid conduit 332 to convey inhibitor from the inhibitor tank 330 to the chamber 102. In some embodiments, the inhibitor tank 330 is configured to store an inhibitor at a set temperature, for example, approximately 4° C.

In some embodiments, the assembly 300 may further comprise a second apparatus 334 comprising a second chamber 336. The second apparatus 334 may also comprise an agitation mechanism 338 for agitation a mixture held or contained in the second chamber 336. The second chamber 336 may be in fluid communication with the port 120 of the chamber 102 of the apparatus 100 via a fluid conduit 340 connected to an inflow port 342 of the second chamber 336. The second chamber 336 may also be in fluid communication with the inhibitor tank 324, the agent tank 324 and/or the air tank 318 via conduits 332, 326 and 334, and 320, respectively, and for example, via fluid conduit 340.

A plurality of flow control valves 344 may be employed to control the conveyance of fluid between the air tank 318, the agent tank 324, the inhibitor tank 330, the chamber 102 of the apparatus 100 and/or the second chamber 336 of the second apparatus 334.

The assembly 300 may further comprise collection receptacle 346 for receiving a mixture from the chamber 102 of the apparatus 100 and/or a mixture from the second chamber 336 of the second apparatus 334. For example, the collection receptacle 346 may be in fluid communication with the chamber 102 and/or the second chamber 336 via a collection conduit 348 and may be in fluid communication with conduit 332. In some embodiments, the collection receptacle 346 may comprise a plurality of compartments 350 which may be configured to receive mixture and/or matter for recycling, collection and/or waste.

Conduits 304, 312, 320, 326, 332, 340 and 348 may each include a channel suitable for conveying fluids, and may, for example, be comprise a tube and/or a pipe.

Figure 4A:
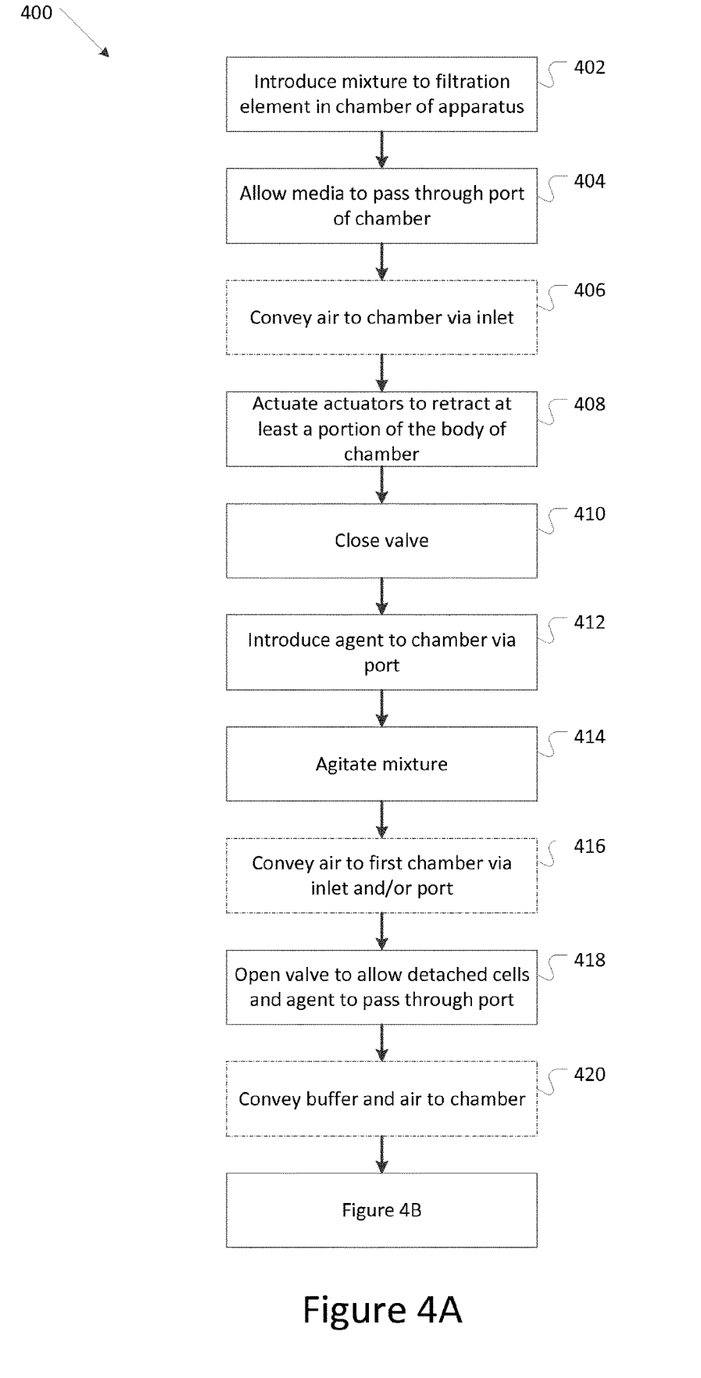
FIGS. 4A and 4B are a process flow diagram of a method of separating cells from microcarriers, according to some embodiments.
Figure 4B:
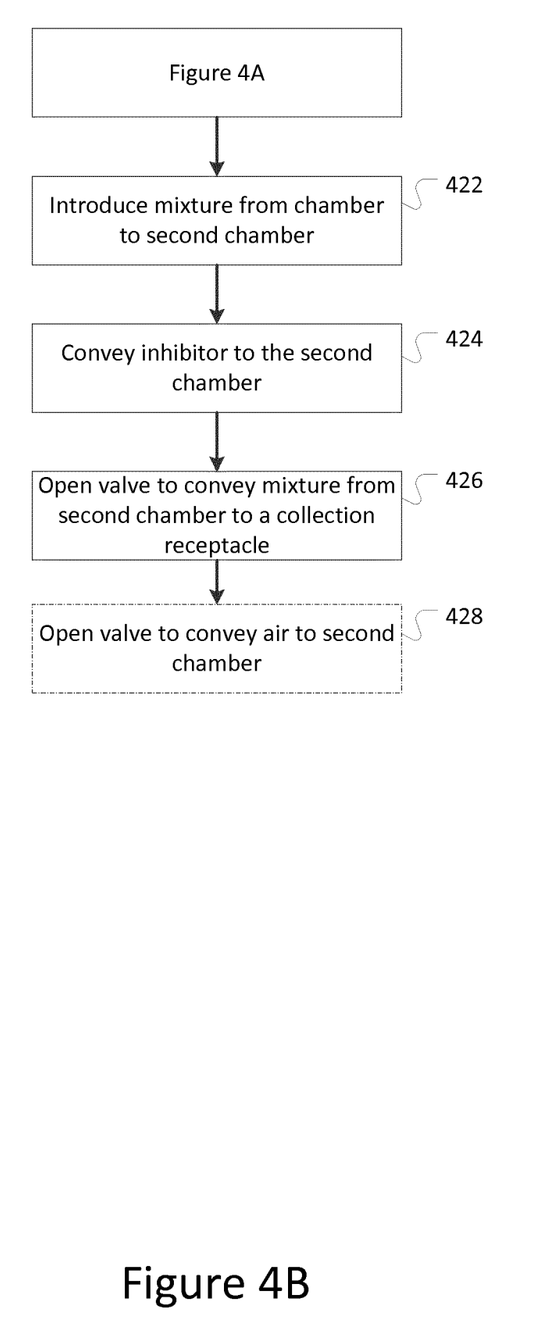

Referring to FIGS. 4A and 4B, there is shown a process flow for a method 400 of separating cells from microcarriers, according to some embodiments. FIGS. 5A to 5F depict schematic views of the chamber 102 of the apparatus 100 and FIGS. 5G and 5H depict schematic views of the second chamber 336 of the second apparatus 334 associated with the method of separating cells from microcarriers of the process flow of FIGS. 4A and 4B.

At 402, a mixture including media, cells and microcarriers is introduced into the filtration element 126 in the chamber 102 of the apparatus 100. The chamber 102 may assume an at least partially or fully extended state, as shown in FIG. 1B, to allow for a greater capacity to receive the mixture. Content of the chamber 102 is preferable maintained at a set temperature, for example, approximately 37° C.

Figure 5A:
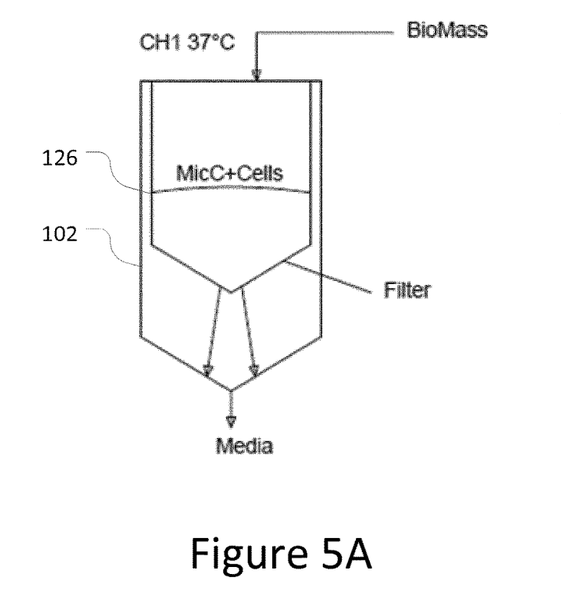
FIGS. 5A to 5F are schematic views of the apparatus of FIGS. 1A and 1B associated with the method of separating cells from microcarriers of FIGS. 4A and 4B.

At 404, the media is conveyed from the chamber 102 via the port 120 provided at the base 110 of the chamber 102 and the cells and microcarriers to which they are attached are filtered by the filtration element 126, as depicted in FIG. 5A.

In some embodiments, the flow control valve 344 disposed at or in a vicinity of port 120 may be opened to allow for the media to be conveyed from the chamber 102 of the apparatus 100. Media conveyed from the first chamber 102 may be conveyed directly, for example, via conduit 332, or indirectly, for example, via the second chamber 336 of the second apparatus 334 and conduit 348, to the collection receptacle 346 or to one of the compartments 350 of the collection receptacle 346. A flow control valve 344 associated with the second chamber 336 of the second apparatus 334 may be opened to allow the media to be conveyed through the second chamber 336 to the collection receptacle 346 or to one of the compartments 350 of the collection receptacle 346 via conduit 348. The flow control valve 344 associated with the second chamber 336 may be closed once the media has been conveyed to the collection receptacle 346 or to one of the compartments 350.

Figure 5B:
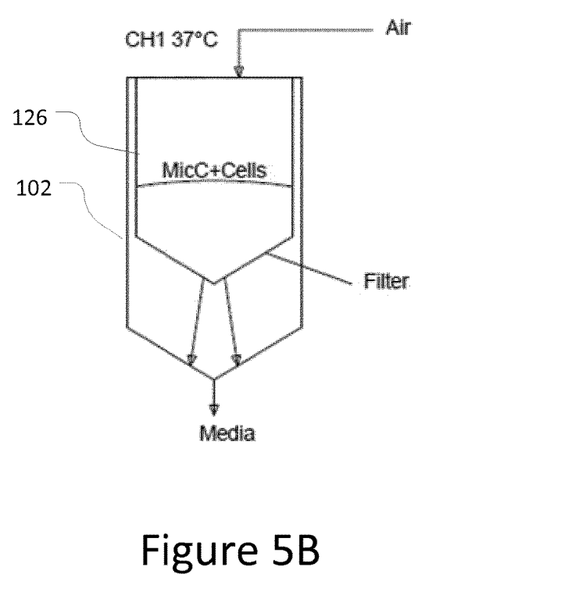

At 406, air from the air tank 318 may be conveyed to the chamber 102 via air conduit 320 to assist in facilitating the conveying of the media from the chamber 102, as depicted in FIG. 5B.

Figure 5C:
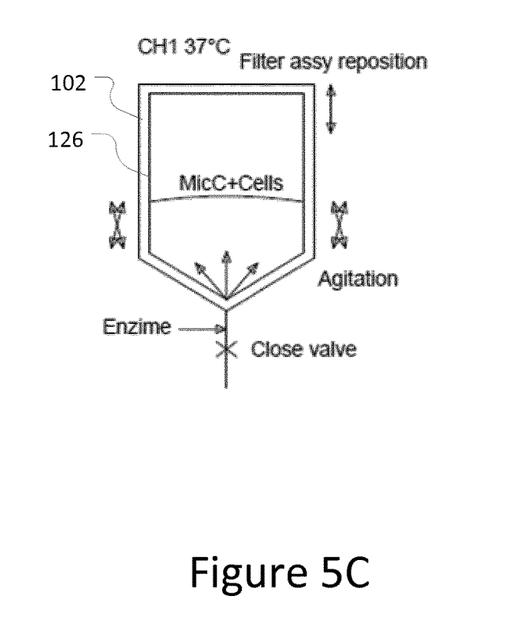

At 408, the adjustment mechanism 104 is actuated to cause the body 108 of the chamber 102 to be retracted or compressed to reduce the capacity of the chamber 102 of the apparatus and to cause the filtration element 126 to move toward the base 110 of the chamber 102. At 410, the flow control valve 344 disposed at port 120 is closed to prevent or block a flow of fluid from the chamber 102, as depicted in FIG. 5C.

At 412, an agent, for example, a detachment agent, is introduced to the chamber 102 so that the filtration element 126 in the chamber 102 includes a mixture comprising the agent, cells and microcarriers. For example, agent may be conveyed from the agent tank 324 via agent conduit 326 and introduced into the chamber 102 via port 120. The agent may propagate or disperse from the base 108 toward the body 106 of the chamber 102. Introducing the agent to the chamber 102 at the base of the chamber may improve penetration of the mixture. The agent is employed to facilitate the detachment or release of cells from microcarriers. At 414, the mixture is agitated using the agitation mechanism 136 to assist with the detachment or release of the cells from the microcarriers.

By actuating the adjustment mechanism 104, the body 106 of the chamber 102 is retracted and the filtration element 126 is moved toward the base 110 of the chamber 102. As a result, the cells and cell carriers are concentrated toward the base of the chamber 102 and an amount of detachment agent required to be introduced into the chamber to cause the detachment of the cells from the microcarriers may be reduced.

Figure 5D:
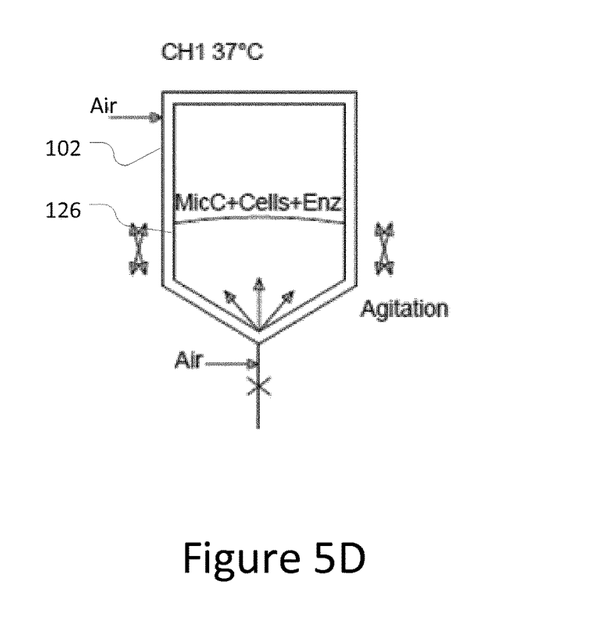

At 416, air from the air tank 318 may be conveyed to the chamber 102 via air conduit 320 to assist in facilitating the mixing of the agent, cells and microcarriers and detachment of the cells from the microcarriers, as depicted in FIG. 5D.

Figure 5E:
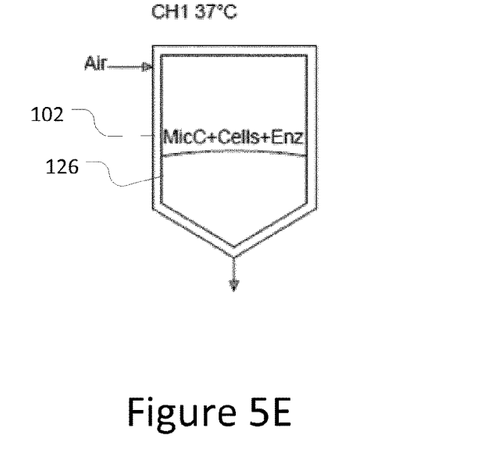

At 418, the flow control valve 344 disposed at port 120 is opened to allow the agent and the cells that have been detached from the microcarriers to be conveyed from the chamber 102, the microcarriers being filtered by and remaining in the filtration element 126. In some embodiments, the agent and detached cells are conveyed to the chamber 336 of the second apparatus 334. In some embodiments, air may be conveyed to the chamber 102 to facilitate the mixing of the agent and the cells from the chamber 102, as depicted in FIG. 5E. For example, air may be conveyed from the air tank 318 to the inlet 118 of the chamber 102 via air conduit 320.

Figure 5F:
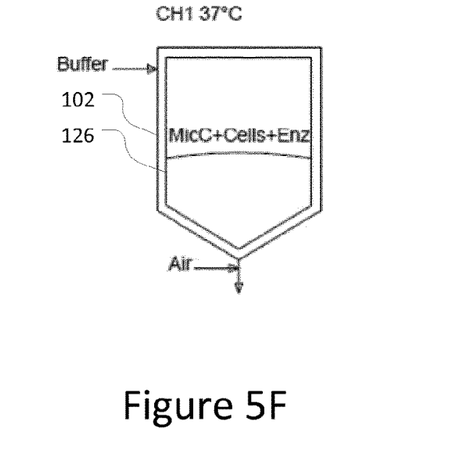
Figure 5G:
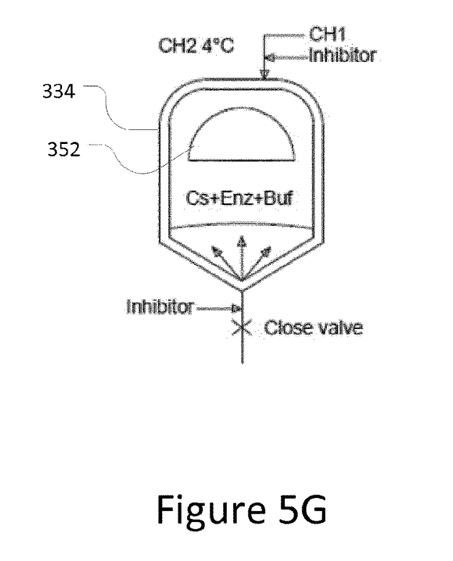
FIGS. 5G and 5H are schematic views of a second apparatus associated with the method of separating cells from microcarriers of FIGS. 4A and 4B.
Figure 5H:
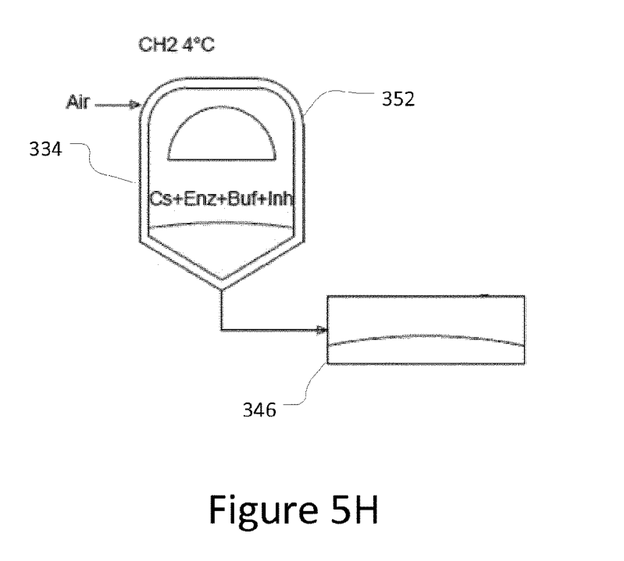

At 420, in some embodiments, buffer and air may be conveyed to the chamber 102 to rinse or flush out the agent and the cells from the chamber 102, as depicted in FIG. 5F. For example, buffer may be conveyed from buffer tank 310 to the port 116 of the chamber 102 via conduit 312 and air may be conveyed from the air tank 318 to the port 120 of the chamber 102 via air conduit 320.

At 422, the buffer, agent and cell mixture is conveyed to the second chamber 336 of the second apparatus 334. In some embodiments, as depicted in FIG. 5G, the second chamber 336 may comprise a valve or diverter element 352 to allow control over a flow of fluids into the second chamber 336. The flow control valve 344 associated with the second chamber 336 may be closed to disallow or prevent the conveyance of the buffer, agent and cell mixture from the second chamber 336 of the second apparatus 334.

At 424, an inhibitor, such as an agent inhibitor, is conveyed to the second chamber to decrease or inhibit the activity of the agent in the mixture. In some embodiments, as depicted in FIG. 5G, the inhibitor may be conveyed from the inhibitor tank 330 to the second chamber 334 via the conduit 332. Content of the second chamber 334 is preferable maintained at a set temperature, for example, approximately 4° C.

At 426, the flow control valve 344 associated with the second chamber 336 is opened to allow the conveyance of the buffer, agent, cell and inhibitor mixture from the second chamber 336 of the second apparatus 334 to the collection receptacle 346. Air may be introduced into the second chamber 336 to assist with the conveyance of the buffer, agent, cell and inhibitor mixture from the second chamber 336 to the collection receptacle 346.

Figure 6A:
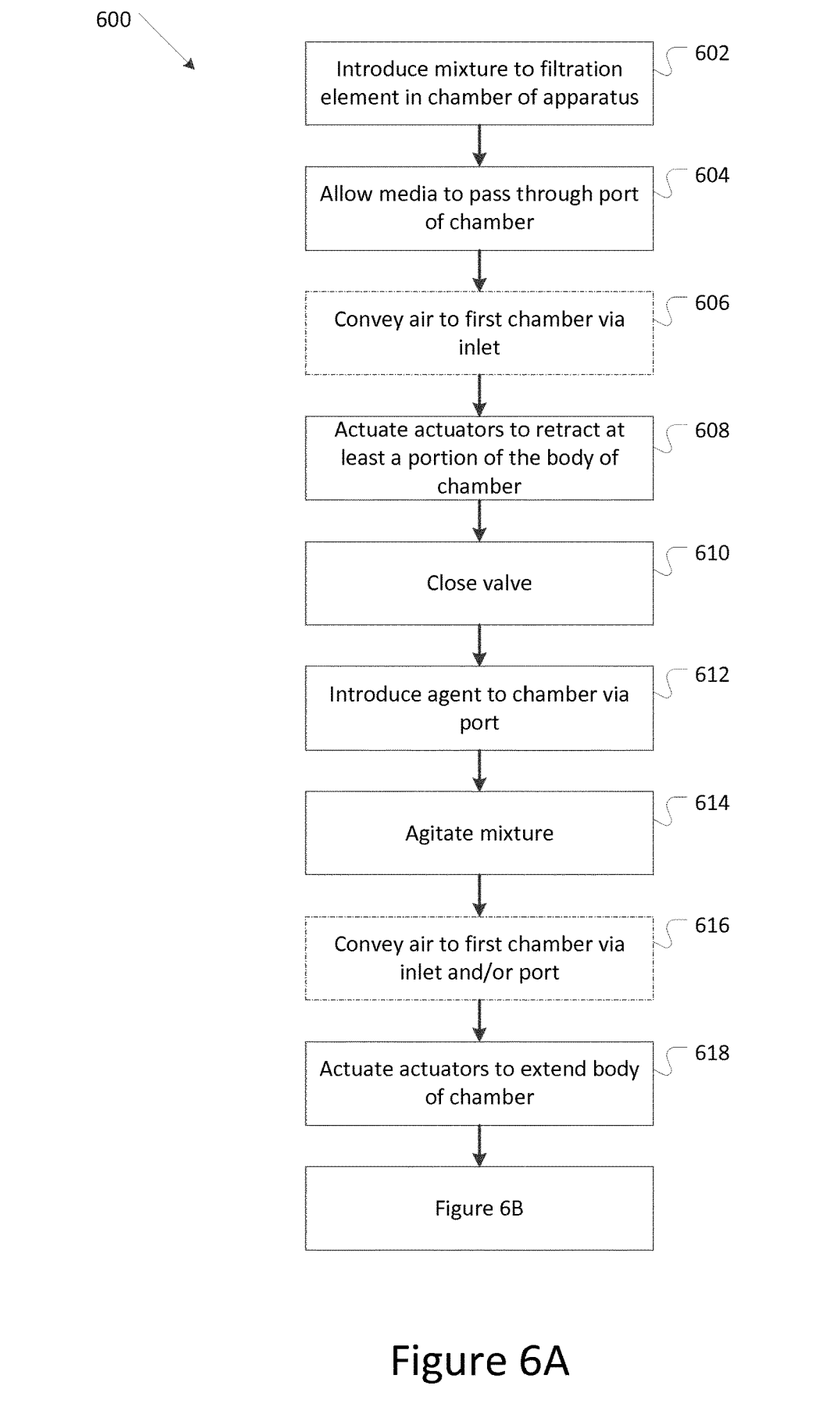
FIGS. 6A and 6B are a process flow diagram of a method of separating cells from microcarriers, according to some embodiments.
Figure 6B:
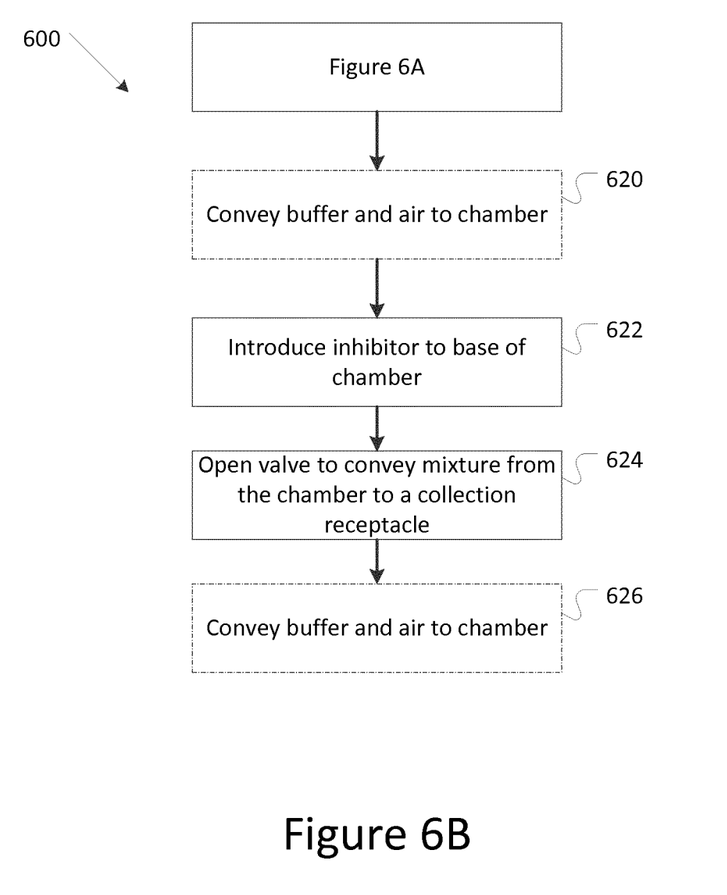

Referring to FIGS. 6A and 6B, there is shown a process flow for a method 600 of separating cells from microcarriers, according to some embodiments. FIGS. 5A to 5D and 7A and 7B depict schematic views of the chamber 102 of the apparatus 100 associated with the method of separating cells from microcarriers of the process flow of FIGS. 6A and 6B.

Steps 602, 604, 606, 608, 610, 612, 614, and 616 of method 600 correspond with steps 402, 404, 406, 408, 410, 412, 414, and 416 of method 400. However, as opposed to transferring the agent and the cells that have been detached from the microcarriers to another vessel or chamber before introducing an inhibitor, method 600 involves introducing the inhibitor to the chamber 102 of the apparatus 100.

Figure 7A:
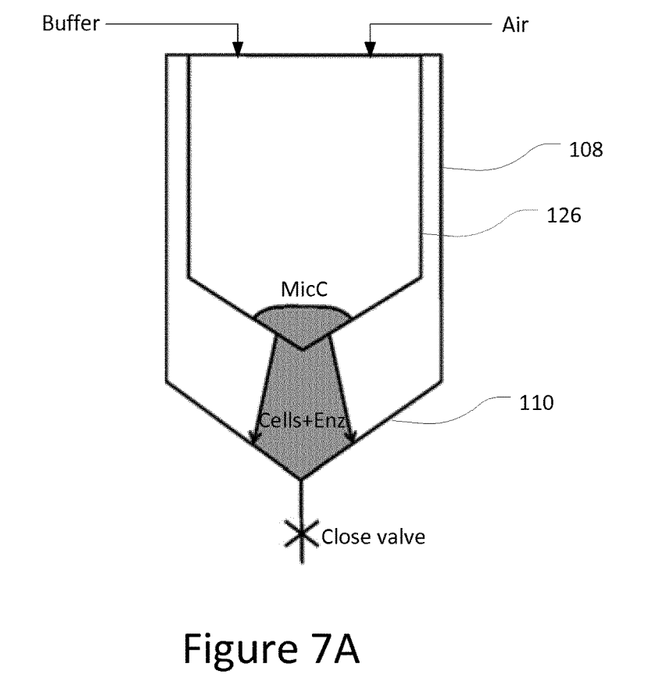
FIGS. 7A and 7B are schematic views of a chamber of the apparatus of FIGS. 1A and 1B associated with the method of FIGS. 6A and 6B.

As depicted in FIG. 7A, at 618, the adjustment mechanism 104 is actuated to cause the body 108 of the chamber 102 to be extended to cause the filtration element 126 to move away from the base 110 of the chamber 102. For example, and as depicted in FIG. 7A, the filtration element 126 is elevated or held at a distance from the base 110 of the chamber 102. The microcarriers may be held in or filtered by the filtration element 126 and the detached cells and agent may pass through the filtration element 126 and may be directed toward or remain at the base 110 of the chamber 102.

At 620, in some embodiments, buffer and/or air may be conveyed to the chamber 102 to rinse the filtration element 126 and chamber 102 and cause the agent and the cells to be flushed through the filtration element 126. For example, buffer may be conveyed from buffer tank 310 to the chamber 102 via conduit 312 and air may be conveyed from the air tank 318 to the inlet 118 of the chamber 102 via air conduit 320.

At 622, an agent inhibitor is introduced to the chamber 102. The agent inhibitor is mixed with the mixture comprising the cells and agent to inhibit the activity of the agent in the mixture. For example, in some embodiments, where the detachment agent comprises an enzyme, the agent inhibitor is an enzyme inhibitor for stopping the reaction of the detachment agent.

Figure 7B:
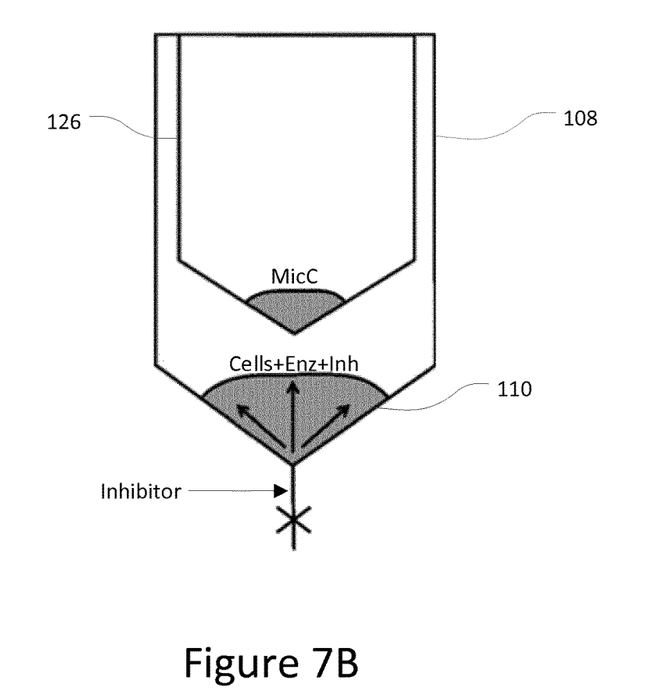

As depicted in FIG. 7B, the inhibitor may be introduced to the chamber 102 of the apparatus 100 via port 120 and the inhibitor may propagate or disperse from the base 110 toward the body 108 of the chamber 102. In some embodiments, introducing the inhibitor to the chamber 102 at the base 110 of the chamber 102 may improve penetration of the mixture. The inhibitor may be conveyed from the inhibitor tank 330 to the chamber 102 via the inhibitor conduit 332. The temperature of the content of the chamber 102 may be reduced and preferable maintained at a temperature of approximately 4° C.

At 624, the flow control valve 344 is opened to allow the conveyance of the mixture including the cells, agent, inhibitor and the buffer, if present, from the chamber 102 of the apparatus 100 to the collection receptacle 346. In some embodiments, air and/or buffer may be introduced into the chamber 102 to assist with the conveying of the mixture from the chamber 102 to the collection receptacle 346.

As discussed in relation to FIGS. 2A and 2B, the apparatus 100 may be employed as a bioreactor apparatus 200. Methods 400 and 600 described above may also be performed using the bioreactor apparatus 200 of FIGS. 2A and 2B as opposed to the apparatus 100. The bioreactor apparatus 200 may be employed to perform cell separation from microcarriers and other bioreactor processes including perfusion and washing. For example, the bioreactor apparatus 200 may be used to exchange pre-set volumes of media during a mixing process. This would allow pre-set volumes of media to be exchanged, for example, added to and/or removed from the bioreactor apparatus 200, without requiring the process to be stopped. Accordingly, the process may be performed continuously. Furthermore, no supplementary equipment would be required to exchange the pre-set volumes of media.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The claims defining the invention are as follows:

1. An apparatus for separating cells from microcarriers, the apparatus comprising:
  a chamber having a body and a base, the body and the base configured to receive a mixture comprising cells and microcarriers;
  a filtration element extending into the chamber and coupled to the body, the filtration element comprising a filtration element base and filtration element side walls and configured to filter microcarriers from the mixture; and
  an actuator coupled to the chamber, the actuator configured for selective extension and retraction of at least a portion of the body of the chamber to move the filtration element relative to the base of the chamber, the filtration element being separable from the base of the chamber.

2. The apparatus of claim 1, wherein selective extension of the at least a portion of the body of the chamber in response to selective actuation of the actuator causes the at least a portion of the body to extend away from the base of the chamber and selective retraction of the at least a portion of the body of the chamber in response to selective actuation of the actuator causes the at least a portion of the body to retract toward the base of the chamber.

3. The apparatus of claim 1, wherein selective extension of the at least a portion of the body of the chamber in response to selective actuation of the actuator causes the filtration element to move away from the base of the chamber and selective retraction of the at least a portion of the body of the chamber in response to selective actuation of the actuator causes the filtration element to move towards the base of the chamber.

4. The apparatus of claim 1, wherein the chamber is configured to transition between an extended state and a retracted state in response to selective actuation of the actuator.

5. The apparatus of claim 1, wherein the filtration element comprises a filter configured to allow cells to pass through the filter and to block microcarriers from passing through the filter.

6. The apparatus of claim 1, wherein the filtration element comprises a filter base configured to cooperate with the base of the chamber to allow the filter base to sit flush with the base of the chamber when the apparatus is in a retracted state.

7. The apparatus of claim 1, wherein the body includes bellows to allow for expansion and contraction of the body.

8. The apparatus of claim 1, wherein the body of the chamber includes a lower portion and an upper portion that is extendible, and selective actuation of the actuator causes the upper portion of the body to expand and to extend away from the base, while the lower portion of the body remains unchanged during said selective actuation of the actuator.

9. The apparatus of claim 1, further comprising a cover coupled to an upper end of the body of the chamber, wherein the filtration element is coupled to at least one of the cover or the upper end of the body of the chamber.

10. The apparatus of claim 1, wherein the filtration element side walls extend into the chamber.

* * * * *